(12) United States Patent
Siegel (10) Patent No.: US 8,335,697 B2
(45) Date of Patent: *Dec. 18, 2012

(54) SYSTEM AND METHOD FOR MONITORING MEDICATION PRESCRIPTIONS USING BIOMETRIC IDENTIFICATION AND VERIFICATION

(75) Inventor: Steven Siegel, Fort Lauderdale, FL (US)

(73) Assignee: Bio-Tech Medical Software, Inc., Fort Lauderdale, FL (US)

( * ) Notice: Subject to any disclaimer, the term of this patent is extended or adjusted under 35 U.S.C. 154(b) by 11 days.

This patent is subject to a terminal disclaimer.

(21) Appl. No.: 12/850,395

(22) Filed: Aug. 4, 2010

(65) Prior Publication Data

US 2010/0299158 A1    Nov. 25, 2010

Related U.S. Application Data

(63) Continuation-in-part of application No. 12/370,204, filed on Feb. 12, 2009, now Pat. No. 8,086,470.

(60) Provisional application No. 61/028,089, filed on Feb. 12, 2008.

(51) Int. Cl.
*G06Q 50/00* (2012.01)

(52) U.S. Cl. ............................................. 705/2; 705/3

(58) Field of Classification Search .................. 705/2, 3; 713/186; 382/115
See application file for complete search history.

(56) References Cited

U.S. PATENT DOCUMENTS

| | | | |
|---|---|---|---|
| 6,711,460 B1 | 3/2004 | Reese | |
| 7,072,738 B2 | 7/2006 | Bonney et al. | |
| 7,415,138 B2 * | 8/2008 | Schneider et al. | 382/115 |
| 7,593,549 B2 * | 9/2009 | Reiner | 382/115 |
| 7,711,583 B2 * | 5/2010 | Epstein et al. | 705/3 |
| 2002/0035484 A1 | 3/2002 | McCormick | |
| 2002/0143582 A1 * | 10/2002 | Neuman et al. | 705/3 |
| 2002/0173875 A1 | 11/2002 | Wallace et al. | |
| 2003/0050799 A1 * | 3/2003 | Jay et al. | 705/2 |
| 2004/0031337 A1 | 2/2004 | Broussard et al. | |
| 2004/0059463 A1 | 3/2004 | Coughlin | |
| 2004/0210341 A1 | 10/2004 | Wallace et al. | |
| 2004/0249497 A1 | 12/2004 | Saigh et al. | |
| 2005/0160052 A1 | 7/2005 | Schneider et al. | |
| 2005/0261940 A1 | 11/2005 | Gay et al. | |
| 2006/0265102 A1 | 11/2006 | Bain | |
| 2007/0005396 A1 * | 1/2007 | Lee | 705/3 |
| 2007/0010910 A1 | 1/2007 | Pinney et al. | |

(Continued)

OTHER PUBLICATIONS

International Preliminary Report of Patentability; Written Opinion of the ISA; PCT/US2009/033006 dated Aug. 17, 2010.

*Primary Examiner* — Gerald J. O'Connor
*Assistant Examiner* — Jonathan K Ng
(74) *Attorney, Agent, or Firm* — Edwards Wildman Palmer LLP; Howard M. Gitten (57) ABSTRACT

This invention is a system and method for a matching system that cross-references patients anonymously with doctors and pharmacies. The invention uses patient-unique biometrics, such as fingerprinting, retinal scanning, or another such unique identifier, for patient identification and verification without revealing a patient's name or other personal information. The system tracks patient prescriptions and produces alerts to indicate potential problems, such as drug interactions or possible fraudulent behavior. The system utilizes the biometric data of the prescribing physician as authorization of the prescription. The system can produce a traceable paper trail, for investigation or prosecution, and protects the medical industry, patients, and the public from the consequences of doctor shopping.

6 Claims, 5 Drawing Sheets

U.S. PATENT DOCUMENTS

| | | |
|---|---|---|
| 2007/0028107 A1 | 2/2007 | Cowburn et al. |
| 2007/0061590 A1* | 3/2007 | Boye et al. .................... 713/186 |
| 2007/0108219 A1 | 5/2007 | Handfeld et al. |
| 2007/0185615 A1 | 8/2007 | Bossi et al. |
| 2007/0191985 A1 | 8/2007 | Bain |
| 2007/0208454 A1 | 9/2007 | Forrester et al. |
| 2007/0208598 A1 | 9/2007 | McGrady et al. |
| 2007/0258626 A1* | 11/2007 | Reiner .......................... 382/115 |
| 2007/0260491 A1 | 11/2007 | Palmer et al. |
| 2008/0015897 A1* | 1/2008 | Moradi et al. .................... 705/2 |

* cited by examiner

SYSTEM AND METHOD FOR MONITORING MEDICATION PRESCRIPTIONS USING BIOMETRIC IDENTIFICATION AND VERIFICATION

CROSS-REFERENCE TO RELATED APPLICATION

This application is a Continuation-In-Part of U.S. patent application Ser. No. 12/370,204 filed Feb. 12, 2009, which claims benefit under 35 U.S.C. §119(e) to U.S. Provisional Application No. 61/028,089 filed Feb. 12, 2008, the disclosure of which is incorporated herein by reference in its entirety.

BACKGROUND AND RELATED ART

The present invention relates to the recording, monitoring, and verification of the prescription, dispensing, and delivery of controlled substances and/or other dangerous prescription medications. In performing these functions, the invention solves a number of important but loosely related problems inherent in today's system for prescribing, dispensing, and delivering controlled substances while having some assurance that multiple medications will not be abused, will not create drug-drug interactions, and will be used only in prescribed amounts as intended for an identified patient. By monitoring drugs that are prescribed and delivered, the invention reduces the chances that legitimate patients may receive combinations of medications that may produce adverse results while also limiting the potential for abuse by substance abusers and those who cater to them.

Existing systems for managing medication prescriptions, while compliant with the Privacy Regulations under the Federal Health Insurance Portability and Accountability Act of 1996 (HIPAA), are vulnerable to confidentiality abuses due to the wide variety of individuals who have access to names, medications and other individually identifiable and personally sensitive health information. Without monitoring systems for narcotics and other dangerous drugs, the medical industry is susceptible to a number of abuses, including doctor shopping, abuse in which a patient can go to several doctors and pharmacies to obtain multiple prescriptions for the same malady. In states that have controlled substance monitoring systems, the incidence of such abuse has declined dramatically. However, even existing monitoring systems have limited means to prevent or monitor fraudulent behavior such as doctor shopping, prescription alteration, prescription forgery, or any number of other illegitimate schemes.

The invention prevents such abuse, but has the added advantage of using patient-unique biometrics, to identify and verify patients and physician-prescribers, and track and monitor their medication prescriptions. In this manner, the system can provide early notice and override false documentation, can catch innocent errors, and can regulate medications without subjecting physicians and pharmacies to the fear of over-regulation or intrusive regulation, allay patient advocate concerns over potential privacy abuses, yet still provide accountability and responsibility to the process as a whole, for both physicians and patients.

BRIEF SUMMARY OF THE INVENTION

The invention is a system and method for monitoring medication prescriptions, tracking which prescriptions have been issued and which have been filled, and maintaining useful information that may be accessed in situations of medical emergency. The invention will maintain anonymity of patient information, and will normally be used in such a manner as to cross reference only an individual's biometric information with an alphanumeric code (A-N code), and with other non-identifying information related to that individual. In a preferred embodiment, the A-N code will be a 10-digit hexadecimal number. Any other identifying information will either be omitted entirely, or may be maintained in remote files, such as billing files, that may kept on local systems accessible only to physicians, local pharmacies, or other entities approved by the individual. Such files may be encrypted, and will not be accessible outside of the local business except upon extraordinary circumstances.

The system identifies potential abuse and other problematic events, such as drug interactions, and generates alerts to notify end users, such as physicians, patients, and pharmacies, of the possible problems with issuing or filling a prescription. In the event of a genuine medical emergency involving an individual, information identifying the individual's treating physician and, in some embodiments, current medications and prescriptions, and any significant medical information, may also be made available to ensure that proper emergency treatment may be administered without unknowingly or inadvertently causing adverse results. The ability of the system to accept, maintain and, in the event of an emergency involving an individual, to release information that can lead to identifying the individual, may be totally precluded or restricted in a number of ways, and may even be subject to the voluntary approval of individuals whose medications would otherwise be tracked anonymously by the system.

The system uses reliable patient-unique biometrics that can be measured quickly with standardized and relatively inexpensive technology, such as fingerprinting, retinal scanning, or other similarly unique identifiers that currently exist or may become available in the future. In a preferred embodiment, fingerprinting the index and middle finger print or, if such is not possible, a standardized protocol of alternate fingers or the hand would be another easily verifiable biometric that could be taken using inexpensive biometric devices, and that could easily be used to help in identifying persons who are unconscious. These biometrics serve as a unique identifier both to match against anonymous medical information, and to allow the determination of the person's identity upon an adequate showing of need, and to verify that the patient is not obtaining additional medications through doctor shopping. For example, standardized devices, such as a 500 dpi fingerprint reading device and other biometric data readers, can be used to measure the biometrics at physician's offices and pharmacies, which can then be securely transmitted to the system together with a prescription or a prescription verification.

The invention may also allow biometrics to be used to identify physicians, pharmacists and others authorized to prescribe or dispense medications. When this is done, fraudulent prescriptions can be detected, and physicians, pharmacists, or others who may be obtaining drugs for unauthorized purposes can be identified, and their activities monitored.

The use of biometrics, rather than a name, social security number, date of birth, address, or other commonly used identifier makes personally identifiable health information much less vulnerable to broad access and misuse. For example, without a "biometric hit" (which requires a patient's personal presence), a pharmacist, pharmacy tech, regulatory investigator or other outsider has no way to access an individual's data on the system. This feature truly limits access to only those individuals with a bona-fide "need to know."

The system can be used also for verification when the prescriptions are to be secured by another on behalf of the patient. In this case, the prescription associated biometric identifier obtained at the client's location must be that of the family member or other person duly authorized to obtain the medication on the patient's behalf.

Telephone prescriptions, which are legal for prescription and Class III through V Controlled Substances, may occasionally occur without opportunity to obtain the biometric at the client's location. These can be made through the assignment of an ID number which can be stored in the system pending the biometric identifier that can be introduced into the system upon dispensing of the medication. The biometric identifier will then be available for all future prescriptions.

The system includes a client program which is installed on local machines and which may involve a two-step login process. In the first step, a secure connection is established by the client program to the system's servers using existing security communication standards, such as an SSL certificate. The client is authenticated by obtaining a username and the biometrics of the user him or herself. The second step is such that, in a preferred embodiment, the local database is encrypted and can be accessed through a username and password sequence, or through some other suitable security implementation.

The local client databases may include a subset of information maintained in one or more databases on the central server, or may also include specific information on patients or other individuals that is useful for local interactions, but that is largely irrelevant for the central server. The local databases can be SQL or any other common database, and can be encrypted such that private data remains secure even if the computer containing the database should be stolen. As thus encrypted, the database can include personally identifiable information, such as patient name, date of birth, and phone number, and a unique identification metric, such as a 10 digit hexadecimal ID number, which identifies the patient to the system. Data from the local databases may be selectively transmitted when specifically authorized to be transmitted to the central server and stored there as well.

The client program can include a graphical user interface, which would display the information, as well as the biometrics read into the client-program. This display will ensure that the biometric was properly read into the system. The client program can also maintain a log of events that have occurred that day and in previous days.

The client program allows medication prescriptions and prescription verifications to be entered, and would include the name of each medication, its strength, quantity, and frequency of being administered. The prescriptions may then be batched and submitted to a single server. Once the prescriptions and verifications have been submitted to the server, the system can use the information to track the length of time a patient should be using a specific medication, and can monitor its proper usage. The system also checks for outstanding medication prescriptions of similar schedules if the prescription is submitted from a medical office. If a pharmacy submits a prescription verification, the system can check for confirmation that a corresponding prescription has been received from a medical office. Regardless of who is submitting a prescription, the system can check for potential drug interactions with other medications that patient is using. If no interactions or conflicts are found, the system sends a confirmation that the prescription or prescription verification was successfully entered. If an interaction or conflict is found, the system sends the client program an alert, which can vary by degree from critical to normal, depending upon the severity of the interaction or conflict.

Normal alerts generally result from mistakes, though may be indicative of mischief. These can occur, for example, when a biometric scan is taken improperly or in a different manner at a pharmacy than at the doctor's office, or when a patient attempts to fill a forged prescription, or when the same doctor prescribes additional medications to a patient who is already on outstanding prescriptions. Normal alerts are issued as warnings, are tracked, and require a password or the entry of biometric data from by an authorized person to force submission, although they generally do not require a confirmation of receipt. These alerts are also stored on the client computer where they can later be retrieved and re-read.

The system tracks the quantity, dosage and prescription instructions and can issue alerts based upon the expected length of time that a patient's supply of the medication will last. Critical alerts include possible drug interactions, attempts to fill a prescription that has already been filled, attempts to get additional prescriptions for schedule II, III, or IV medications from a second doctor while taking medication prescribed or dispensed by a first doctor. Critical alerts also require the original owner or authorized user of the client-program installation to provide a password or biometric data and confirmation that the alert has been received. The alert is stored in the local database, and will restore itself and persist until acknowledged, even if the client computer is shut down. The system keeps track of the "Alert received" confirmation and stores it in both the central server, and on the client computer where it can later be retrieved and re-read.

Some critical alerts may have multiple recipients, such as alerts for a patient attempting to get additional medication from a second doctor. In such a case, critical alerts can be sent to both doctors, in which case each will receive the other's contact information and the unique patient identification metric (patient ID Number).

Other embodiments of the invention can include varying degrees intermediate alerts.

The system may also include a patient registration system which allows a patient to enter personal data into the system. In a preferred embodiment, this personal information will be stored on the local system only, and will not be transmitted to the central server. The patient registration system may be used to educate the patient on the risks of misusing prescriptions, the laws against such behavior, and can confirm the user's understanding of the risks and laws. The patient registration system may also include other questionnaires to educate the patient, monitor the patient's treatment and medication usage, and help diagnose problems that the patient may have. The patient registration system may be implemented to use biometric identification, or may use other means of identification (driver's license, social security number, etc.).

The invention method is the process that begins when patient information, which may include a patient-unique biometric, is entered into a local database. This can be done where such information is normally gathered and stored, such as at a doctor's office or hospital, either by office or hospital staff, or by the patient via a direct patient registration system. The patient information is transmitted to a central server where it is matched to a patient identification metric (usually an ID number); or if it is a new patient, a patient identification metric is generated for the patient.

Next, the doctor's office may enter medication prescriptions together with the patient's biometric data into the system, as described above. The system will check for conflicts and drug interactions. If none are found a confirmation of the prescription information is sent back to the doctor's office, but if conflicts or interactions are found an alert is sent back to the doctor's office. Alerts are handled and stored in the manner described above.

When the patient tries to fill the prescription, the pharmacist will enter a prescription verification into the system, together with the patient's biometric data, as described above. If the prescription has not yet been filled, and no other alerts are triggered, a confirmation is sent. If an alert is triggered it is handled and stored in the manner described above.

Once a prescription has been filled as described above, if the patient then goes to another doctor or pharmacy to obtain a new prescription, or to fill a prescription that has already been filled, the appropriate alerts will be sent to the appropriate client systems.

Notification that a prescription has been filled and delivered may also be sent to the treating physician or other prescribing entity. Such notification can assist in discovering forged prescriptions, since the entity to whom a prescription is attributed may be notified that a prescription that it did not prepare has been filled. Such notification may also be beneficially used to alert a prescribing physician that a patient has not yet received a prescribed medication, and thereby trigger inquiries from the physician to the patient.

This invention allows for confirmation that prescriptions are genuine and accurate, and ensures that the patient can fill only prescriptions that are issued only once. In this manner the invention prevents doctor shopping and prescription forgery, eliminates fraud through identity theft, and identifies schedule II, III, IV and V patients without infringing on privacy, while providing a paper trail to document wrongdoing.

This invention also permits the monitoring and tracking of prescriptions to the same individual being filled by different pharmacies. In this case, if a patient were to obtain a medication from a pharmacy and then attempted to obtain additional medication from another pharmacy, The system would determine whether an alert should be generated and, if so, would require appropriate notifications to be generated.

Accordingly, it is an object of the present invention to provide a system and method for managing medication prescriptions using biometric data. It is another object of the invention to provide a system and method for preventing fraud in filling medical prescriptions. It is another object of the invention to provide a system and method for increasing the accountability of physicians and pharmacists when making and filling prescriptions. It is another object of the invention to prevent dangerous drug interactions occurring across multiple prescriptions. These, as well as other objects, will become apparent by consideration of the detailed description of the preferred embodiments and the accompanying drawings.

DESCRIPTION OF THE INVENTION

Figure 1:
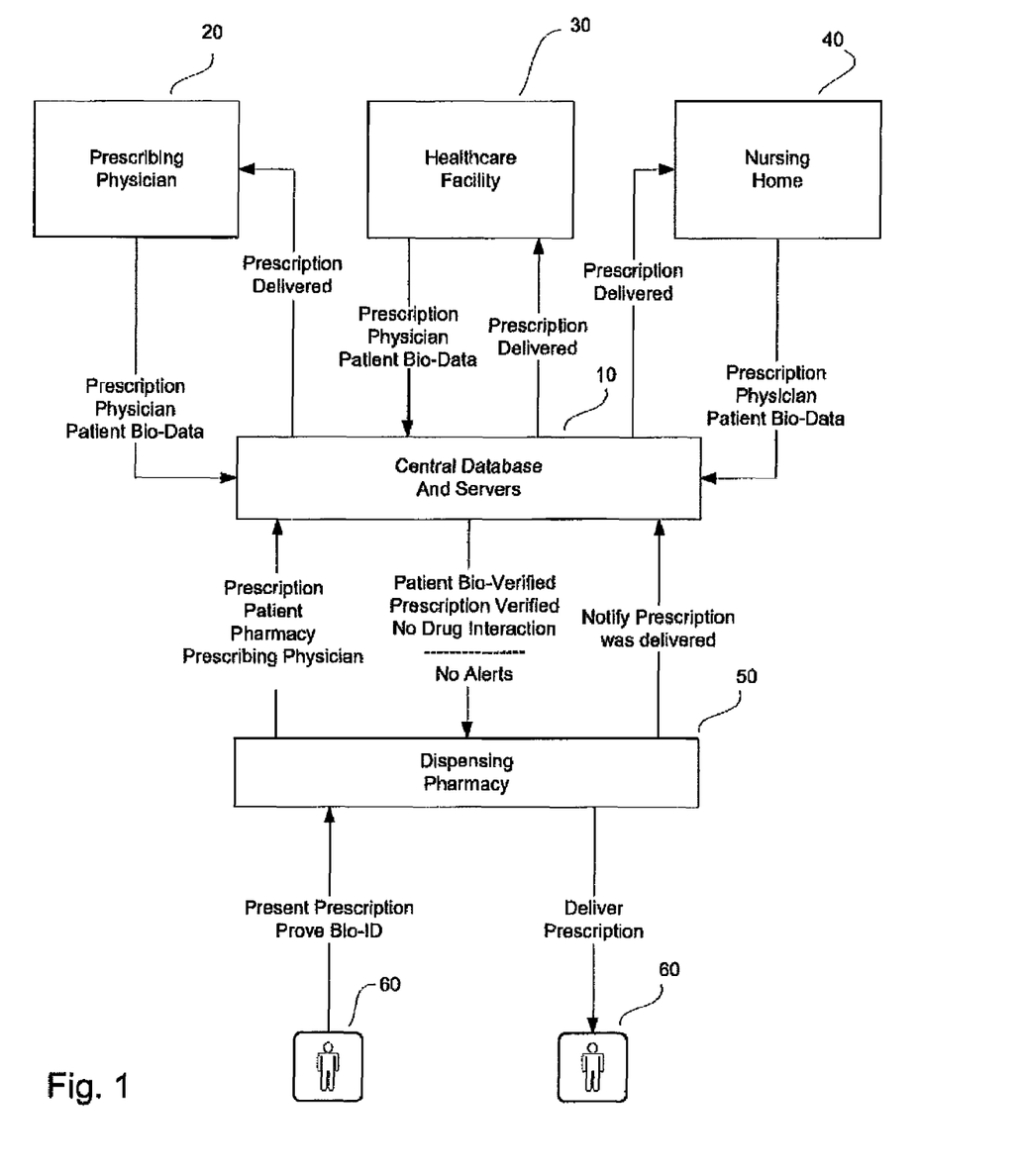
FIG. 1 is a conceptual chart showing the components of the invention and their respective interactions.

As is depicted in FIG. 1, an overview of the invention includes a central server where information is processed and stored 10, and a number of peripheral sites connected to the central server where information is received or disseminated. Information entered by a prescribing physician 20, a healthcare facility 30, or a nursing home or other similar provider 40 will include, at a minimum, the name and quantity of the drug or medication, the identity and contact information of the prescribing physician, and a biometric identifier that is unique to the patient. The prescription record may also include a text box where notes regarding the prescription or the patient's use of it may be recorded. This information will be processed and stored, cross-referenced against an alphanumeric identifying code, preferably a 10-digit hexadecimal number that is randomly assigned, until the prescription is presented to a dispensing pharmacy 50 or other dispensing facility for filling.

When the prescription is presented for filling, the pharmacy 50 will obtain a unique biometric identifier from the person presenting the prescription 60, and will forward that identifier, plus the prescription information (name and quantity of the drug or medication) and the identity of the prescribing physician or entity to the central server 10. An analysis will be done to determine whether the patient's immediate prescription and other prescriptions indicate overuse, or abuse, of the prescribed medication or family of related medications. An anomaly in this check may be indicative of a drug abuser, or a provider of controlled substances to others. Upon verifying that the prescription and the presenter are legitimate, the server will signal the pharmacy that there are no alerts, whereby the prescription may be dispensed.

Figure 2:
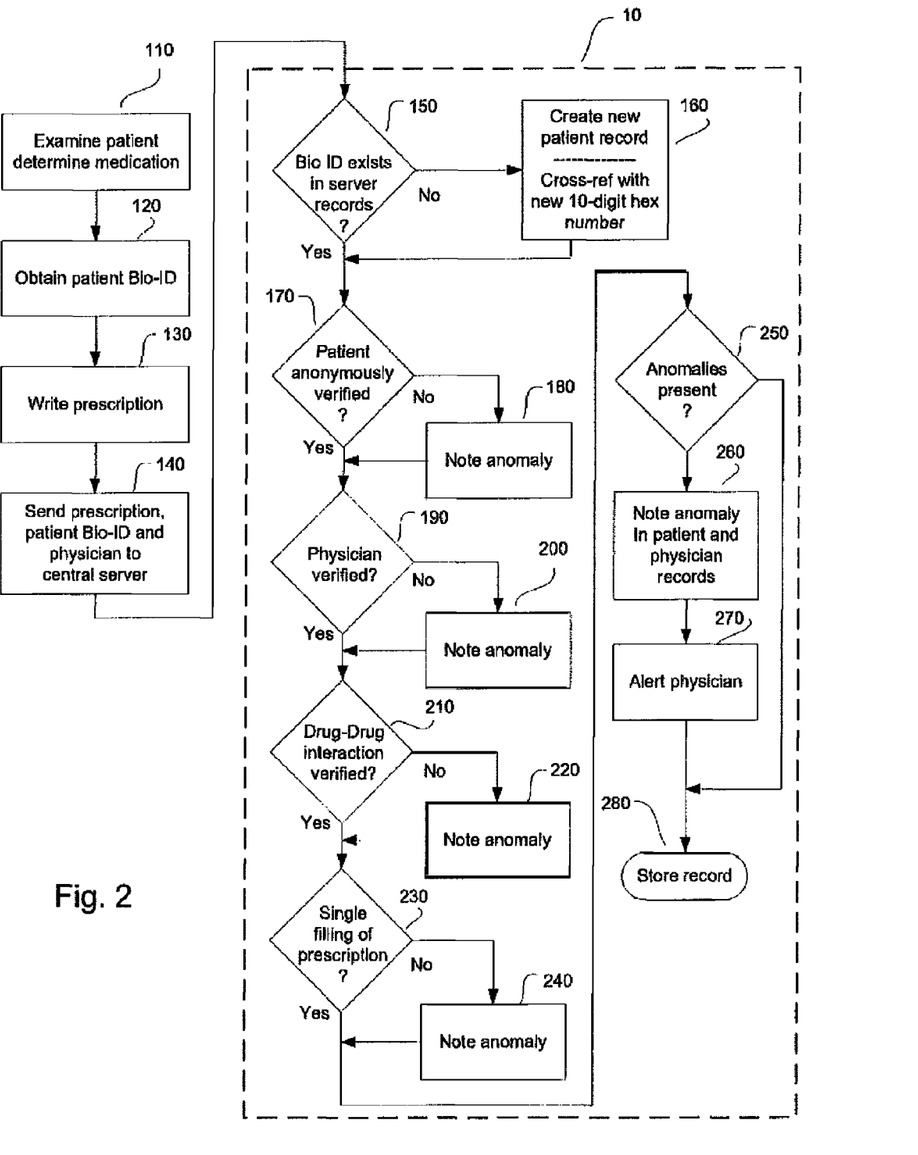
FIG. 2 is a flow chart showing the procedure for entering a prescription into the central server.

FIG. 2 illustrates an exemplary depiction of how a prescription record will be created at the central server. A physician or other person authorized to prescribe prescription drugs will determine that a patient is in need of a particular medication 110. The patient's biometric identifier (BioID) will be taken at the physician's office and converted to a computer data file 120. The prescription will be written and a physical copy handed to the patient 130. The physician's office will also electronically send the prescription (drug name and quantity) to the central server, along with the patient's BioID and the physician's identity 140. As discussed below, the physician's identity may include a BioID either alone or in combination with other identifying information. This information may be encrypted where security of the information is a concern, and will be encrypted in a preferred embodiment of the invention.

At the server, the information is decrypted. Following decryption a number of checks will be performed to ensure that the prescription is appropriate and able to be filled. In no particular order, the system will perform each check, noting any anomalies that may be detected and recording them along with the prescription record.

In the embodiment depicted in FIG. 2, the BioID data is compared to all the biometric data previously issued into the system 150. If this is the first time this individual's fingerprint has been entered into the system, a unique alphanumeric identifier code (A-N code) is linked to the just received data, and this becomes the permanent primary identifier for this individual in the system 160. In the preferred embodiment, the A-N code will be a 10-digit hexadecimal number that may be randomly or pseudo-randomly generated, and that will be unique for each patient. If that individual's fingerprints have been previously entered, then the new data is linked with that already in the system, and a processor analyzes the data for any signs of prescription alteration, doctor shopping, over-prescribing, drug-drug interactions, etc. Any issues or problems identified will generate an alert back to the entering facility as well as to any providers, pharmacists or facilities previously associated with this particular individual.

Another validation check 170 will reference the A-N code to determine whether there are any flags or adverse information associated with the patient. For example, if the patient has died, or has been convicted of criminal activity related to procuring, selling, or abusing drugs, or some other adverse information associated with the A-N code is present, an anomaly will be generated 180 and associated with the prescription record. Various levels of anomalies may be implemented, and an overall assessment of the record will be made before the record is stored or approval to dispense can be given.

Another validation check is made to verify that the physician is legitimately authorized to dispense drugs of the kind named in the prescription 190 or conversely that the prescription is authorized by a physician. In this case, if there is no reason why the physician should remain anonymous, the physician may be identified by name or other indicator that can be cross-referenced to identify the physician. Checks at this level may verify that the physician is alive, that he or she is authorized to prescribe the drug named in the prescription, and that no other adverse information is associated with that physician that would prevent him or her from prescribing the drug. In cases in which the forgery of a physician's name is suspected, or a physician's computer is likely to have been compromised, or in which a higher level of security is desired, the system may also call for the physician to submit a BioID to verify his or her identity and the authorization of the prescription. In a preferred embodiment, should the physician's biometric be required, it will normally be included in each patient's prescription record, although other methods of transmitting the physician's identifying biometric may also be used, such as requiring a second physician identifier (e.g. PIN) with each prescription, or only a single biometric to be submitted when prescriptions are batched and submitted to the central server in a single transmission, session, or file. Any anomalies in verifying the physician will be noted 200 and added to the prescription record.

It follows, that the physician BioID may be used as an authorization or digital signature for the prescription. If a controlled substance is prescribed, central server 10 will prompt the prescribing physician 20 to authenticate the prescription. In order to complete the prescription, prescribing physician 20 will provide their BioID to central server 10 as discussed in connection with step 190 above. Central server 10 will compare the submitted physician BioID with biometric data stored at central server 10. If no anomalies are detected in step 200 then the process continues and central server 10 creates a digital signature to travel with the prescription to dispensing pharmacy 50 as described further below.

It should be noted that it is well within the scope of the invention that the creation of the digital signature be performed at a local computer, such as in the prescribing physician office or at the hospital. It is also contemplated that prior to creation of a digital signature, a secondary authorization technique be used such as a personal identification number (P.I.N.), a private key known to the physician, or, even if unknown to the physician such as a token, belonging only to the physician or the like. The digital signature and/or authorization is then stored at central server 10 as part of the archived record involving the specific prescription. It should also be noted that it is within the scope of the invention that the authorization may be applied to prescriptions in batch. The authorization may be done first to begin the validation check discussed herein, or as a last step after any anomalies have been accounted for.

A drug-drug interaction check will also be made that cross-references the drug named in the prescription with other drugs prescribed for the same patient 210, taking into account both the dose sizes of respective medications and the times during which the patient is expected to be taking each of the medications. This information will be analyzed, and potential adverse drug-drug interactions will be noted 220.

Another validation check will be done to determine whether the patient has previously filled, or attempted to fill, the same or a similar prescription 230. The results of this check may indicate that a patient is "doctor shopping," or is engaging in some other unauthorized activity to obtain more of the prescribed medication than the prescription allows. The analysis of the single-prescription validation check will take into account the possibility that the patient is on a long term medication regime, and will not generate false anomalies if a prescription is simply repeated from time to time, as long as the dosage and frequency of filling are consistent with the prescription, and the prescription is legitimately renewed from time to time. Anomalies noted in the prescribing of multiple prescriptions will be noted 240 and added to the prescription record.

Other relevant checks or verifications may be conducted during processing of the prescription received from an authorized prescription writer. After checks have been completed, any anomalies noted will be analyzed 250. In the vast majority of cases it is anticipated that no anomalies will have been noted, and the prescription record can be passed to storage on the central server 280. Where anomalies have been noted, however, they will be processed 260 and stored in relevant records of the prescribing physician or the patient, as appropriate, and one or more alerts may be generated 270. In the majority of cases in which an anomaly has been noted, an alert will be sent to the prescribing physician. Where two physicians have prescribed medications that may cause adverse interactions, both physicians will receive alerts.

There may be rare instances in which the entry of a prescription into the system of the invention may indicate that criminal activity is taking place. Although the system is designed to follow the real-world model in which physicians and pharmacists have discretion whether or not to notify authorities of the likely presence of criminal activity, it is also capable of being configured to trigger an alert to law enforcement authorities when the analysis of anomalies reaches a similar conclusion. In a preferred embodiment, the information transmitted from the central server to authorities in such cases would consist of the names and contact information of both the dispensing and prescribing facilities and the ten digit hexadecimal code associated with the set of biometric data in question. Any other information identifying the individual in question would be maintained on local machines and would not be provided by the central server. The decision whether to implement the criminal-reporting feature is one appropriately made by governmental authorities who may use the system.

Figure 3:
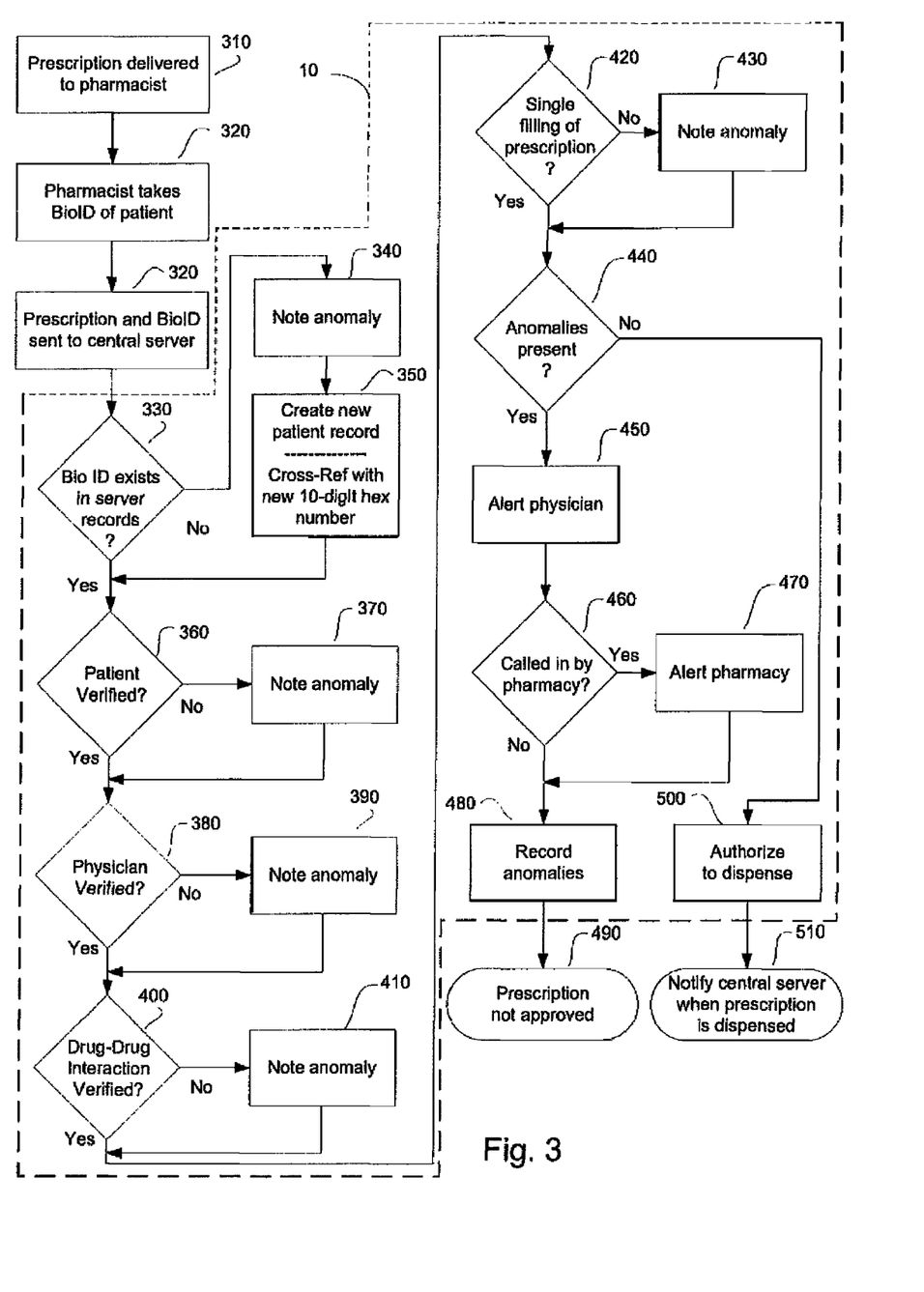
FIG. 3 is a flow chart showing the steps for a patient to deliver a prescription to a pharmacy and the steps taken to verify and dispense the prescription.

FIG. 3 depicts an exemplary flow chart demonstrating the steps for filling a prescription. The patient, having received a prescription from a physician or some other person authorized to write prescriptions, presents it to a pharmacy to be filled 300. The pharmacist will verify the identity of the patient by taking the patient's BioID at that location 310. This information will be entered into the system at a computer terminal, together with the prescribing information on the prescription, and any relevant comments, will be entered in a text box. The software will encode the biometric data and then encrypt that data along with the prescribing information, any text comments, and the identity of the provider or pharmacy entering the data into the system. Of note is that neither the patient's name nor other identifying information such as social security number is transmitted to the server. The prescription, the patient's BioID, and the name of the pharmacy are then sent to the central server 320 where a series of checks will be made to verify the accuracy and propriety of the prescription.

As noted in connection with the initial entry of a prescription into the central server, the order of steps taken by the central server is not critical, and the sequence depicted in FIG. 3 is exemplary rather than mandatory. The central server will check the patient's BioID for a match 330. Even if the patient has not previously filled a prescription, there should be a matching BioID and physician digital signature that was furnished by the prescribing physician. If there is no matching BioID, an anomaly is noted 340 and a new patient record is created and cross referenced with an A-N code 350. Under these circumstances, the most likely cause of there being no match is that the physician's office has not yet submitted the prescription information to the central server or the prescribing physician is not participating in the system. If this should be the case, an alert may be sent to the physician 450 and the anomaly may be corrected.

In both the physician's office and the pharmacy situations in which a patient's BioID is to be taken and submitted to the central server, an embodiment of the invention requires that the biometric scanning unit be connected directly to the central server. This precaution eliminates the potential for human error or malicious intervention, and provides security that the BioID taken on-site is the same computer file that is being sent to the central server.

The central server will verify the patient 360 using the A-N code from the patient table, and will note any anomalies relating to the patient 370. The prescription record including any appended anomalies will checked to verify the authorization of the physician 380. The check will confirm the digital signature and proceed as described earlier, and any anomalies will be noted 390. If the system is so configured, a biometric identifying the physician may also be checked in step 380.

The prescription will also be checked for drug-drug interaction 400, and anomalies will be noted 410. A related check to ensure that the prescription has not already been filled 420 will be performed, with any anomalies being noted 430. Upon the completion of verification checks, the existence of anomalies will be determined 440 and, if no anomalies are present, the submitting pharmacy will be authorized to dispense the prescription 500. Upon actually dispensing the prescription 510, the pharmacy may notify the central server of that fact.

In the event that anomalies are present, the system will alert the prescribing physician and any physicians who have prescribed interacting drugs or the same drug during the same timeframe 450, notifying them of the nature of the anomaly and identifying the prescription. If the prescription was presented through a pharmacy 460, the pharmacy will also be alerted to the nature of the problem 470. In many cases it is anticipated that minor mistakes in prescriptions, or in a patient's BioID, may be cleared up quickly and easily. For example, if a pharmacy's biometric scanner malfunctions, or sends a BioID that cannot be matched with an A-N code, the problem might be remediable simply by having the patient re-scan the biometric and be verified in real time when the prescription is to be dispensed.

In the event that a drug-drug interaction is present, or a potential abuse of drugs is suggested, the pharmacy may be denied authorization to dispense the prescription without the direct intervention of the prescribing physician or some other qualified physician who is authorized to intervene. The patient will also be given verbal or written alerts by the pharmacy. In all cases, the record of the prescription, whether dispensed or not, will be recorded by the central server.

As with other systems, the system of this invention is subject to mistakes based upon human error. In a preferred embodiment, the system will have a designated administrator or administration board whose function is to establish policy, set parameters for anomaly reporting and triggering of alerts, and to correct or update records as anomalies are explained or obviated by subsequent events.

Figure 4:
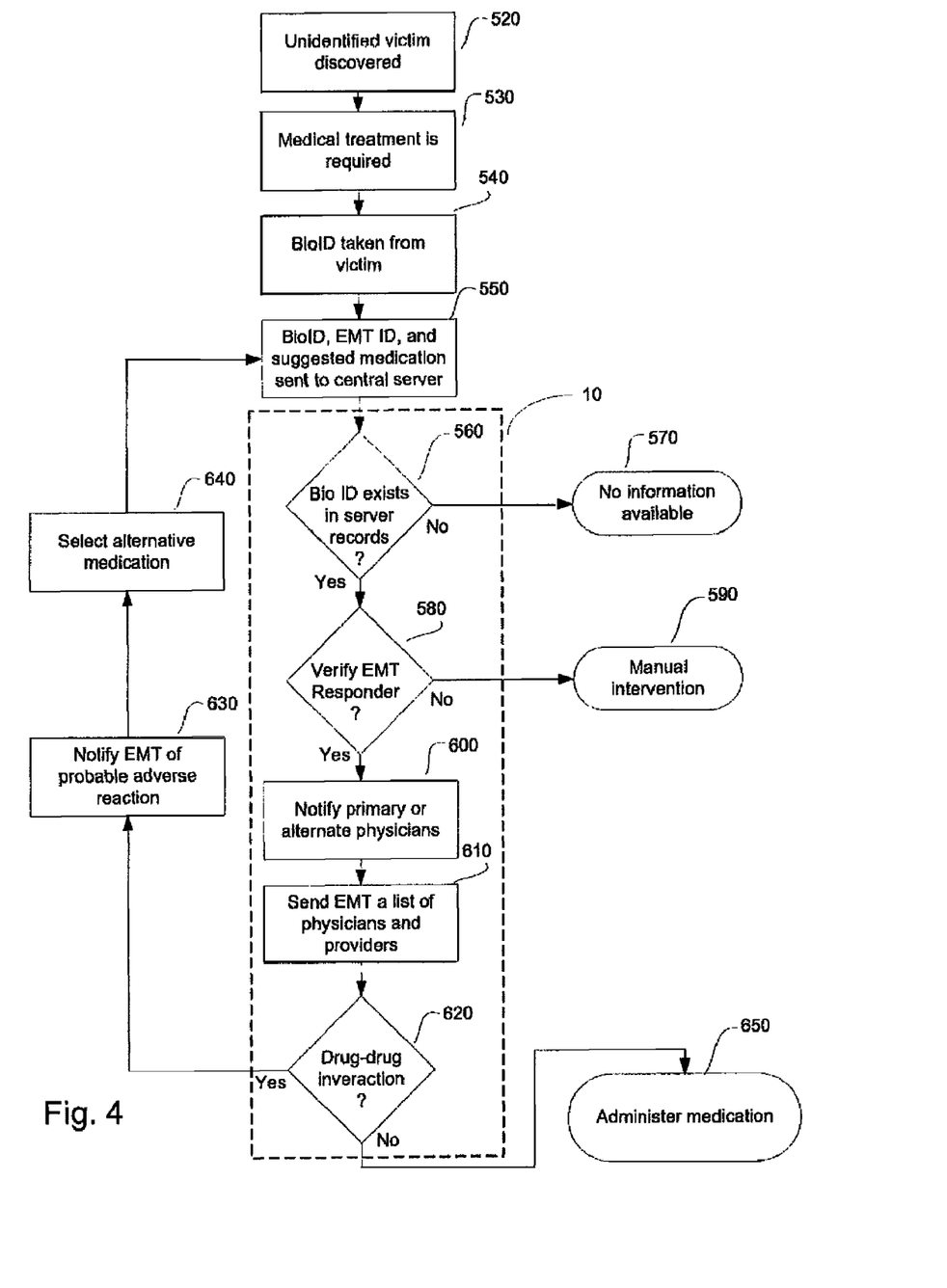
FIG. 4 is a flow chart illustrating the steps an EMT first provider would take before administering a specific medication to an emergency victim.

In an embodiment depicted in FIG. 4, the system may be used to assist emergency medical teams (EMT) to assist persons in severe distress and in need of medical care. In order to use this system to facilitate the recovery of information on an individual in an emergency situation while still maintaining the confidentiality of patient identity and information, it should be noted that, in the preferred embodiment, the server does not contain information to directly identify the individual and does not contain any medical records other than what has been submitted as described above.

As illustrated in FIG. 4, upon the discovery of an unconscious unidentified victim 520, a paramedic or similar responder would enter the biometric data into a portable handheld device which would format the biometric data and encrypt it 540. This information along with the identity, location and contact information of the emergency responder would then be transmitted securely to the server and tagged as "emergency response mode" 550. The central server, upon receiving the encoded and encrypted data would then decrypt the biometric data and compare it with all the biometric data previously entered into the system 560. If that individual has never been entered into the system, the emergency responder would be immediately notified of such 570.

In the case where the victim had been previously entered into the system, the server would then transmit a list of providers, facilities and pharmacies that had previously submitted into the system the biometric data on this individual 610. It would also send an emergency alert to those facilities that had been submitted this patient's biometric data into the system for emergency notification 600. Contact information would be included in these notifications and it would be up to the individuals and facilities to communicate, access and transmit any relevant and needed information.

If EMT personnel should determine that medical treatment is required 530, information identifying the EMT and suggested medication for the victim 550 may be submitted to the central server 10. If a match is found, a check to verify that the EMT responder is legitimate may be made 580. If the EMT responder cannot be verified, the possibility of a fraudulent call should be considered, and manual intervention may be exercised 590. If the EMT is verified, the patient's primary or alternate physician will immediately be notified of the victim's situation 600 and a list of the victim's physicians and providers will be sent to the EMT 610. In one embodiment, the victim's primary or alternate physician may be notified even if the EMT cannot be verified, although the decision when such notification should be given may be subject to subsequent empirical evidence of the number of false or unwarranted calls made to the system. The EMT's suggested medication can be checked for a drug-drug interaction 620, or for abuse (in the case of a fraudulent EMT identification), and if there is no adverse interaction, the EMT may be notified that the suggested medication may be administered 650. If an adverse reaction is indicated, the EMT will be notified 630 and may suggest a different medication and resubmit the necessary information 640 in an attempt to get a clearance to use the alternative suggested medication. In this embodiment, the system does not authorize the dispensing of a prescription, but simply provides information that may help to avoid the administration of medication that could cause an adverse reaction in the victim.

Figure 5:
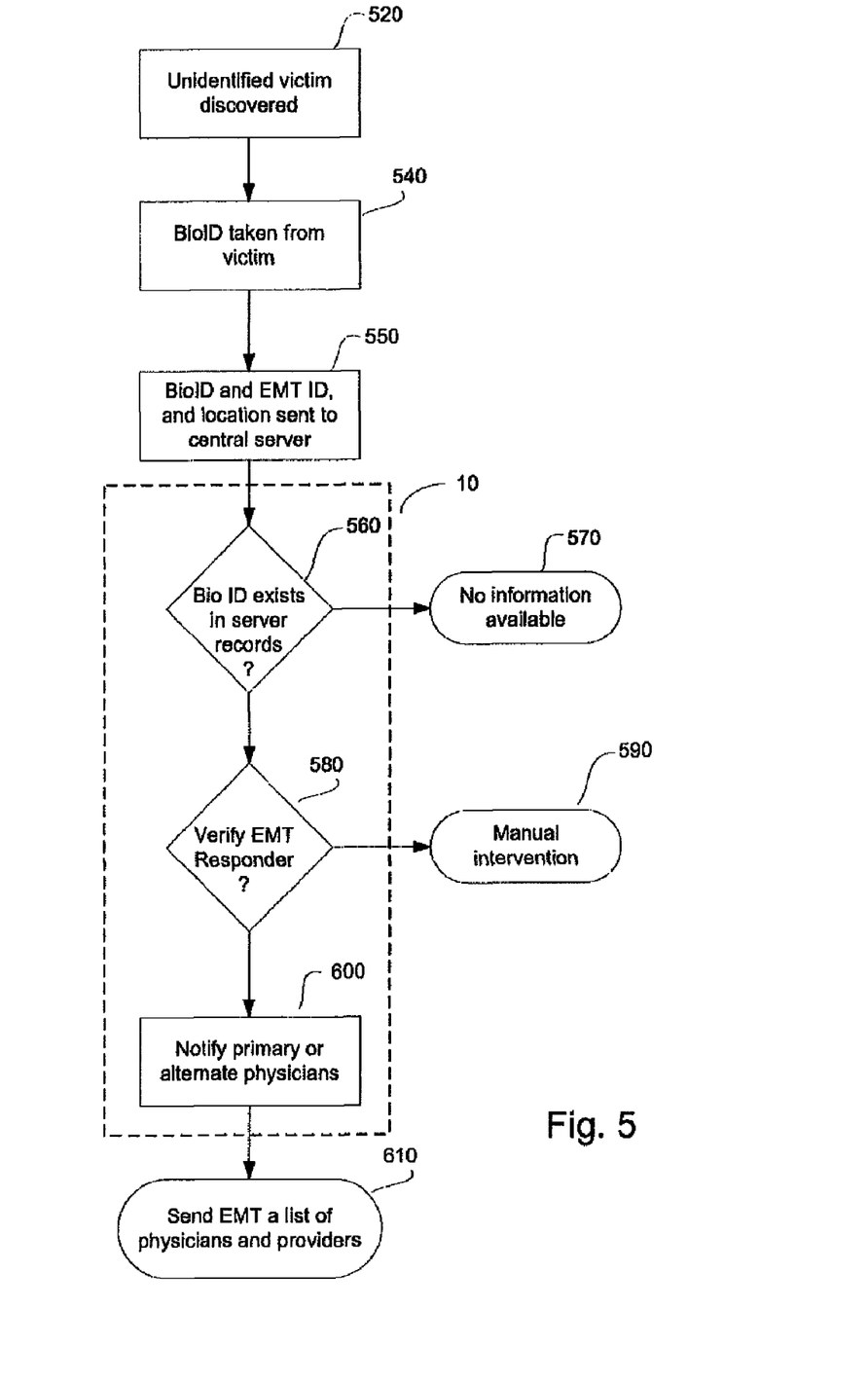
FIG. 5 is a flow chart depicting the steps an EMT first provider would take upon discovering an unconscious victim to ensure notification of the victim's primary physician.

FIG. 5 depicts an embodiment in which a victim's BioID is used solely for purposes of reaching the victim's primary or alternative physicians. In this scenario, there is no drug or prescription verification, but simply an attempt to reach a physician having direct knowledge of the victim or access to the victim's medical records.

In addition to a patient's records including information regarding present medications, an embodiment of the invention can also include information regarding a patient's allergic reactions to certain medications. A query relating to adverse allergic reactions could be incorporated into the drug-drug interaction query, and the results would be handled in the same manner.

It will be understood by persons having skill in the relevant arts that the illustrations and descriptions herein are exemplary and not limiting, as the invention is defined only by the scope of the following claims.

What is claimed as new and desired to be protected by Letters Patent of the United States is:

1. A system for managing controlled substance prescriptions comprising:
    a central server having a processor, said central server having tables comprising a database for receiving, processing, and storing prescription information and non-identifying patient information, the central server cross referencing the non-identifying patient information only to at least one of a patient's biometric data and an alphanumeric number;
    a computer network, said network providing electronic communications between said central server and one or more computers;
    at least one pharmacy connected to a first computer, said computer being connected to said computer network;
    a biometric reader reading identifying biometric data from a physician writing a prescription; and
    at least a second computer communicating with said biometric reader and recording prescription information into said second computer and cross-referencing said prescription information with said biometric data from the physician and creating an authorization associated with the prescription as a function of at least the biometric data from the physician, the authorization being part of the prescription information; the second computer communicating said prescription information to said central server across said computer network; the processor of the central server processing said prescription information with said non-identifying patient information and said at least one of the patient's biometric data and the alphanumeric number at said central server to determine whether said prescription should be filled, and communicating the result of said determination across said network to said first computer.

2. The system of claim 1, wherein said authorization is a digital signature.

3. The system of claim 1, wherein the at least second computer receives at least a second identifying characteristic associated with the doctor to create the authorization.

4. The system of claim 1, wherein the authorization is associated with at least a second prescription.

5. The system of claim 1, wherein said biometric reader reads identifying patient biometric data from a patient associated with the prescription, the biometric data being part of the prescription information.

6. The system of claim 5, further comprising:
    a second biometric reader located at said pharmacy, and communicating with the first computer;
    said second biometric reader reading identifying patient biometric data from a patient, the first computer communicating the patient biometric data to the central server; and
    the central server cross referencing the patient biometric data with said prescription information.

* * * * *